US007706860B2

United States Patent
McGee

(10) Patent No.: US 7,706,860 B2
(45) Date of Patent: Apr. 27, 2010

(54) AUTOMATED MANIPULATION OF IMAGING DEVICE FIELD OF VIEW BASED ON TRACKED MEDICAL DEVICE POSITION

(75) Inventor: David L. McGee, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 835 days.

(21) Appl. No.: 11/117,021

(22) Filed: Apr. 28, 2005

(65) Prior Publication Data

US 2006/0247520 A1 Nov. 2, 2006

(51) Int. Cl.
*A61B 5/00* (2006.01)
(52) U.S. Cl. ....................... 600/424; 600/407
(58) Field of Classification Search ................ 600/407, 600/424, 426–429; 128/899; 702/150–153
See application file for complete search history.

(56) References Cited

U.S. PATENT DOCUMENTS

| 5,255,680 | A | 10/1993 | Darrow et al. |
| 5,377,678 | A | 1/1995 | Dumoulin et al. |
| 5,383,874 | A | 1/1995 | Jackson et al. |
| 5,391,199 | A | 2/1995 | Ben-Haim |
| 5,485,849 | A | 1/1996 | Panescu et al. |
| 5,494,042 | A | 2/1996 | Panescu et al. |
| 5,833,621 | A | 11/1998 | Panescu et al. |
| 6,101,409 | A | 8/2000 | Swanson et al. |
| 6,216,027 | B1 | 4/2001 | Willis et al. |

(Continued)

FOREIGN PATENT DOCUMENTS

EP 0 894 473 2/1999

(Continued)

OTHER PUBLICATIONS

PCT International Search Report for PCT/US2006/016466, Applicant: Boston Scientific Scimed, Inc. , Forms PCT/ISA/210 and 220, dated Sep. 6, 2006 (6 pages).

(Continued)

*Primary Examiner*—Brian Casler
*Assistant Examiner*—Peter Luong
(74) *Attorney, Agent, or Firm*—Vista IP Law Group LLP

(57) ABSTRACT

Methods and systems for navigating medical devices are provided. A patient is imaged while a medical device is moved within the patient. A position (e.g., a location and/or orientation) of the moving medical device is detected within a coordinate system (e.g., a three-dimensional coordinate system), a position of the imaging field of view relative to the patient is adjusted based on the detected medical device position, such that the relevant tissue region of the patient is within the field of view. For example, the field of view can be centered over the medical device or centered just distal to the medical device portion. The direction of view may be oriented at an angle perpendicular to the axis of the medical device, e.g., for more accurately measuring the length of objects within the field of view, or oriented at an angle parallel to the axis of the medical device portion, e.g., for more accurately measuring the diameter of the channel (e.g., blood vessel) in which the medical device is disposed.

49 Claims, 5 Drawing Sheets

U.S. PATENT DOCUMENTS

| | | |
|---|---|---|
| 6,233,476 B1 | 5/2001 | Strommer et al. |
| 6,484,118 B1 | 11/2002 | Govari |
| 6,619,838 B2 | 9/2003 | Bencini et al. |
| 6,711,429 B1 | 3/2004 | Gilboa et al. |
| 6,740,083 B2 | 5/2004 | Messing et al. |
| 7,215,990 B2 * | 5/2007 | Feussner et al. ............. 600/424 |
| 2004/0044279 A1 * | 3/2004 | Lewin et al. ................ 600/407 |
| 2004/0097805 A1 | 5/2004 | Verard et al. |
| 2004/0097806 A1 | 5/2004 | Hunter et al. |

FOREIGN PATENT DOCUMENTS

| | | |
|---|---|---|
| EP | 1523 951 | 4/2005 |
| WO | 97/29682 | 8/1997 |
| WO | WO 97/29709 | 8/1997 |
| WO | 2004/021910 | 3/2004 |

OTHER PUBLICATIONS

PCT Written Opinion of the International Search Authority for PCT/2006/016466, Applicant: Boston Scientific Scimed, Inc., Form PCT/ISA/237, dated Sep. 6, 2006 (5 pages).

PCT International Preliminary Report on Patentability (Chapter I of the Patent Cooperation Treaty) for PCT/US2006/016467, Applicant: Boston Scientific Scimed, Inc., Form PCT/IB/326 and 373, dated Oct. 30, 2007 (6 pages).

PCT International Preliminary Report on Patentability (Chapter I of the Patent Cooperation Treaty) for PCT/US2006/016466, Applicant: Boston Scientific Scimed, Inc., Form PCT/IB/326 and 373, dated Oct. 30, 2007 (6 pages).

* cited by examiner

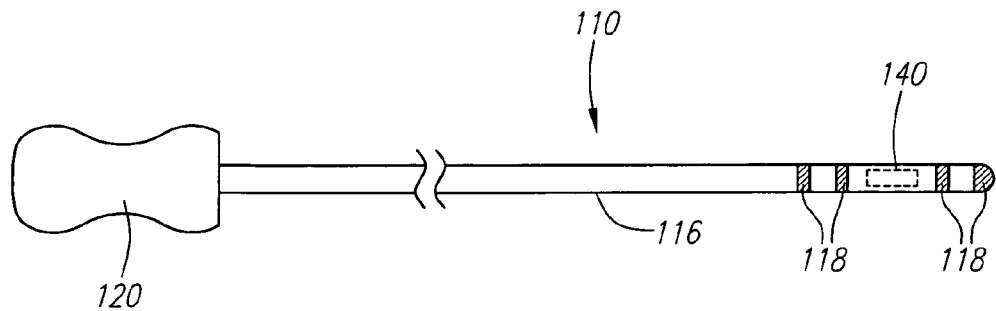
FIG. 2
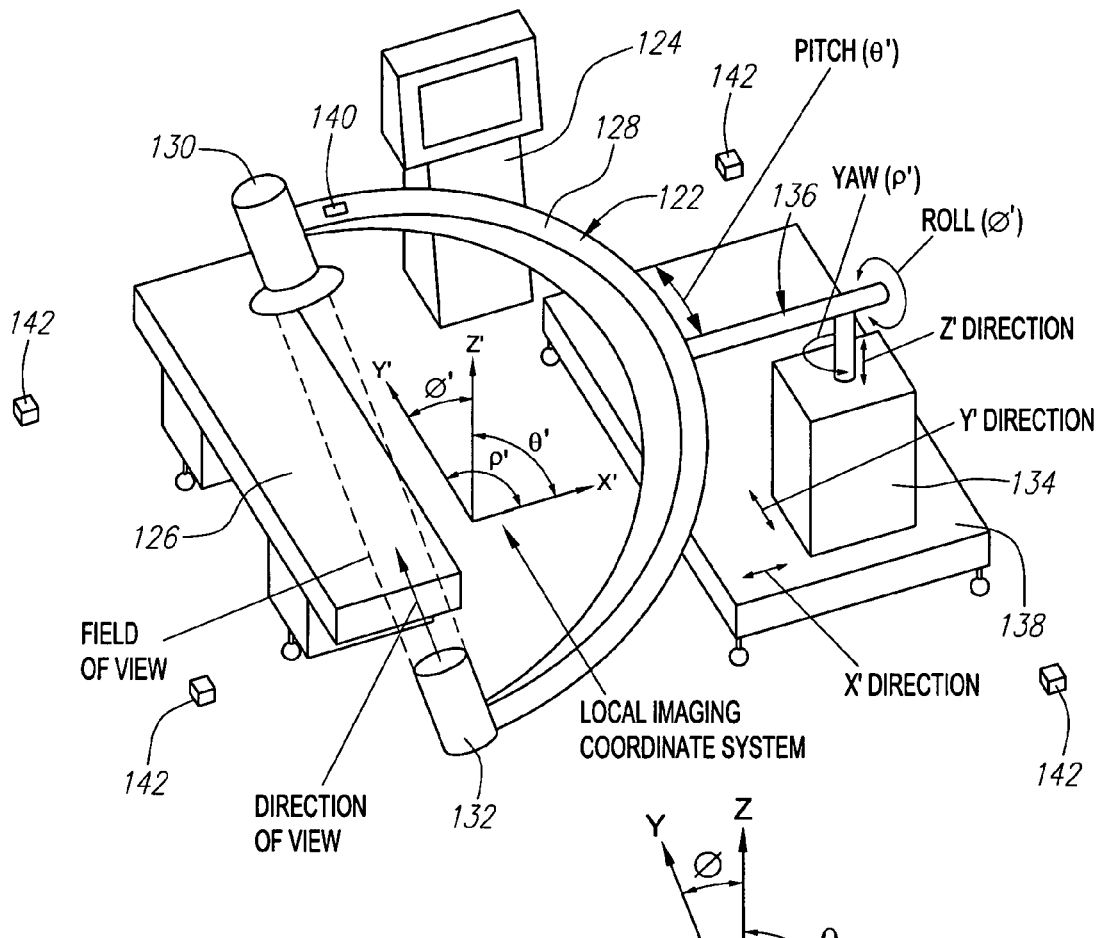
FIG. 3
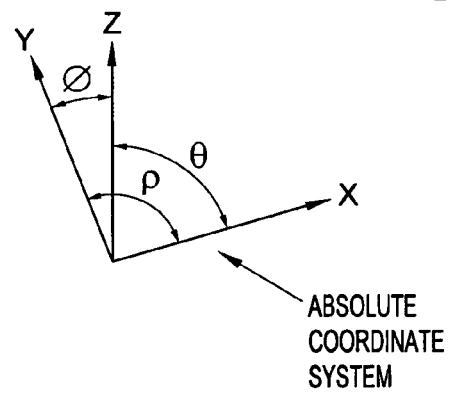

AUTOMATED MANIPULATION OF IMAGING DEVICE FIELD OF VIEW BASED ON TRACKED MEDICAL DEVICE POSITION

FIELD OF THE INVENTION

The present inventions generally relate to systems and methods for navigating medical probes within anatomical organs or other anatomical structures.

BACKGROUND OF THE INVENTION

It is often necessary or desirable to determine the location of a medical probe relative to a location of interest within three-dimensional space. In many procedures, such as interventional cardiac electrophysiology therapy, it is important for the physician to know the location of a probe, such as a catheter (especially, a therapeutic catheter), relative to the patient's internal anatomy. During these procedures, a physician, e.g., steers an electrophysiology (EP) mapping catheter through a main vein or artery into the interior region of the heart that is to be treated. The physician then determines the source of the cardiac rhythm disturbance (i.e., the targeted cardiac tissue) by placing mapping elements carried by the catheter into contact with the heart tissue, and operating the mapping catheter to generate an EP map of the interior region of the heart. Having identified the targeted cardiac tissue, the physician then steers an ablation catheter (which may or may not be the same catheter as the mapping catheter above) into the heart and places an ablating element carried by the catheter tip near the targeted cardiac tissue, and directs energy from the ablating element to ablate the tissue and form a lesion, thereby treating the cardiac disturbance.

To facilitate the navigation of medical devices, such as mapping/ablation catheters, within the patient's body, various types of three-dimensional medical tracking systems (e.g., the Realtime Position Management™ (RPM) tracking system, marketed by Boston Scientific Corporation and described in U.S. Pat. No. 6,216,027 and U.S. patent application Ser. No. 09/128,304, entitled "A Dynamically Alterable Three-Dimensional Graphical Model of a Body Region," and the CARTO EP Medical system, marketed by Biosense Webster and described in U.S. Pat. No. 5,391,199) have been developed, or at least conceived. In these medical systems, the position of the catheter can be determined within a three-dimensional coordinate system. Based on this positional information, a three-dimensional computer-generated representation of a body tissue (e.g., a heart chamber), along with a graphical representation of the catheter or a portion thereof, can be generated and displayed. In the case where a mapping catheter is tracked, electrical activity information can be acquired by the catheter and superimposed over the graphical representation of the tissue in the form of an electrical activity map.

To some extent, real-time three-dimensional tracking systems, such as the RPM and CARTO systems, have reduced the usage of real-time imaging modalities, such as fluoroscopy, during operative procedures. This is because the use of fluoroscopy in locating catheters is somewhat limited in that the physician is only able to visualize the catheter and surrounding tissues in two dimensions. In addition, fluoroscopy does not image soft tissues, making it difficult for the physician to visualize features of the anatomy as a reference for the navigation. Thus, fluoroscopy is sub-optimal for the purpose of navigating a catheter in three-dimensional space, e.g., within the heart. The use of fluoroscopy is also limited in that it poses the danger of exposing the patient and laboratory personnel to harmful doses of radiation.

Despite its limitations, the use of fluoroscopy is still used to generate real-time images of the relevant portions of patients' bodies during various medical procedures or portions thereof. For example, during medical procedures, such as angiography or angioplasty, fluoroscopy is often used to track catheters through the patient's vasculature to the targeted region, e.g., within a selected coronary vessel or chamber of the heart. In the case of interventional cardiac electrophysiology therapy, fluoroscopy can even be used in conjunction with real-time three-dimensional tracking systems, such as the RPM or CARTO systems. In particular, fluoroscopy may be used during the catheterization process (presumably before a graphical representation of the heart is even generated) to ensure that the catheter is introduced through the proper vessels and into the desired chamber of the heart, as well as to confirm proper placement of the catheter adjacent the intended anatomical structure within the heart. Also, because fluoroscopic images are capable of capturing dynamic conditions in real-time, fluoroscopy can also be used to confirm stability of the catheter within the heart, which is especially important during a tissue ablation procedure.

In any event, when an imaging modality, such as fluoroscopy is utilized, the operator (e.g., a physician, nurse, or technician) is typically required to manipulate the imaging system (or the position of the patient's body relative to the imaging system) in order to "aim" the imaging energy at the portion of the patient's body of which the image is desired at any given point in time. For example, in order to acquire the desired fluoroscopic images during a cardiac catheterization procedure, the operator must manipulate the position of the fluoroscope (which typically comprises a C-arm on which the x-ray source and detection components are mounted) relative to the patient (e.g., by moving the fluoroscope and/or moving the table on which the patient lies), such that the most relevant portion of the patient's body is imaged at any given time. For example, as the catheter is moved within the patient's vasculature, it is frequently necessary to periodically adjust the position of the fluoroscope relative to the patient, so that the catheter remains within the field of view of the fluoroscope. Furthermore, it may be necessary for the operator to adjust the orientation of the fluoroscope relative to the patient, such that the fluoroscopic image is generated from a particular point of view. For example, during a catheterization procedure, a physician may desire a fluoroscopic view that is perpendicular to the axis of a blood vessel to facilitate accurate measurement of the length of a vascular lesion or stenosis.

Unfortunately, manual adjustment of the position of an imaging system relative to the patient can be time consuming, difficult, labor intensive, imprecise, and inconvenient. Furthermore, because it may be necessary to visualize a real-time image to determine how to properly adjust the position of the imaging system, this manual adjustment process can lead to prolonged operation of the imaging system. This, in turn, may lead to increased radiation exposure (in the case of fluoroscopy) to the patient and/or medical personnel and may lead to premature failure or degradation of the imaging system due to extended operational time (i.e., components may wear out sooner). Manual adjustment may also not allow the degree of positional accuracy that may be desired. Lastly, because of the radiation danger associated with fluoroscopy, it is desirable to operate the fluoroscope only when it is needed. However, because it is often difficult to predict when fluoroscopic images of the relevant region should be generated, e.g., when a catheter becomes unstable, the fluoroscope may not always be operated when it is most needed.

There thus remains a need for an improved system and method for manipulating an imaging system, such as a fluoroscope, in a manner that facilitates imaging of only the relevant regions of a patient's body at the relevant times.

SUMMARY OF THE INVENTION

The present inventions lend themselves particularly well to the fluoroscopic imaging of tissue for navigating intravascular catheters within a patient, but can be used with other imaging modalities, such as Magnetic Resonance Imaging (MRI), Computed Tomography (CT), positron tomography (PET), and ultrasound, and can be used to image and navigate intrabody medical devices, including, but not limited to, intravascular catheters within the patient.

In accordance with a first aspect of the present inventions, a method of navigating a medical device within a patient is provided. The method comprises imaging the patient within a field of view, moving the medical device within the patient, and detecting a position (e.g., a location and/or orientation) of the moving medical device within, e.g., a three-dimensional coordinate system. In one method, the distal end of the medical device is tracked, although other portions of the medical device may be tracked. In another method, the coordinate system is an absolute coordinate system, and the patient is imaged within a local imaging coordinate system, in which case, the method may further comprise registering the local imaging coordinate system and absolute coordinate system.

The method further comprises automatically adjusting a position of the field of view of an imaging device relative to the patient based on the detected medical device position. The field of view position may, e.g., be continuously adjusted, or intermittently adjusted (e.g., on-demand). In one method, the field of view position may be adjusted relative to the patient by adjusting the field of view position relative to a fixed point. However, the field of view position may also be adjusted relative to the patient by adjusting the position of the patient relative to a fixed point. The field of view position is preferably adjusted, such that the relevant tissue region of the patient is within the field of view. For example, the field of view can be centered over the medical device portion or centered just distal to the medical device portion. An optional method comprises moving another medical device within the patient, detecting a position of the other moving medical device, and automatically adjusting the field of view relative to the patient further based on the other detected medical device position (e.g., by centering the field of view over the geometric center of the distal ends of the medical devices).

In one method, the patient is imaged along a direction of view that is oriented at an angle perpendicular to the axis of the medical device portion. This may be useful, e.g., for more accurately measuring the length of objects within the field of view. In another method, the patient is imaged along a direction of view that is oriented at an angle parallel to the axis of the medical device portion. This may be useful, e.g., for more accurately measuring the diameter of the channel (e.g., blood vessel) in which the medical device is disposed. In one method, the field of view position is adjusted mechanically, e.g., when using fluoroscopy. However, the field of view position may alternatively be adjusted electronically, e.g., when using electronically-steered ultrasound.

Although the present inventions should not be so limited in their broadest aspects, the automatic adjustment of the field of view position obviates, or at least minimizes, manual adjustment of the imaging modality, thereby decreasing the procedure time, and reducing radiation exposure. Also, because the field of view is automatically adjusted to cover only the relevant tissue, the radiation footprint may be reduced, thereby further decreasing radiation exposure and potentially reducing the cost of the imaging device. An optional method comprises activating the imaging based on the detected position of the medical device portion. In this manner, imaging may be performed only when needed, e.g., when the medical device is moving or becomes unstable, thereby further decreasing radiation exposure.

In accordance with a second aspect of the present inventions, a medical navigation system is provided. The system comprises a tissue imaging device having a field of view, an intrabody medical device, a tracking subsystem (e.g., a non-fluoroscopic navigation system) configured for detecting a position (e.g., a location and/or orientation) of the medical device, and an imager positioning subsystem configured for adjusting a position of the field of view (e.g., mechanically and/or electronically) relative to a patient based on the detected position of the medical device. The imager positioning subsystem can be configured for continuously adjusting the field of view, or intermittently adjusting the field of view position (e.g., on-demand). As with the previously described method, the adjustment of the field of view based on the position of the medical device facilitates the imaging of only relevant tissue.

The imager positioning subsystem may be configured for adjusting the field of view position relative to the patient by adjusting the field of position relative to a fixed point or adjusting the position of the patient relative to the fixed point. In one embodiment, the imager positioning subsystem is configured for centering the field of view adjacent the medical device, e.g., over a portion of the medical device or just distal to the medical device. In an optional embodiment, the system comprises another intrabody medical device, in which case, the tracking subsystem is configured for detecting the position of the other medical device, and the imager positioning subsystem is configured for adjusting the field of view position based further on the other detected medical device position, e.g., by centering the field of view over the geometric center of the distal ends of the medical devices. The imager positioning subsystem may optionally be configured for orientating the direction of view of the imaging device at an angle perpendicular to an axis of the medical device, or at an angle parallel to an axis of the medical device. In an optional embodiment, the system further comprises an imager activating subsystem configured for activating the imaging device based on the detected position of the medical device, thereby providing an additional benefit of imaging the tissue only during relevant times. In another optional embodiment, the imaging device has a local imaging coordinate system, and the tracking subsystem is configured for detecting the position of the medical device within an absolute coordinate system, detecting a position of the imaging device within the absolute coordinate system, and registering the local imaging coordinate system and absolute coordinate system based on the detected imaging device position.

In accordance with a third aspect of the present inventions, an imaging system is provided. The imaging system comprises a tissue imaging device, such as the imaging device described above, a processor configured for determining a desired position of the field of view based on a detected position of an intrabody medical device, and a controller configured for adjusting the position field of view relative to a patient in accordance with the desired field of view position. The desired field of view position can be determined and the field of view adjusted in the same manner described above.

In accordance with a fourth aspect of the present inventions, a method of controlling an imaging procedure is provided. The method comprises introducing a medical device within a patient, and detecting a position (e.g., location and/or orientation) of the medical device within the patient relative to a reference position (e.g., a previously detected position of the medical device or a position within a desired path). In one method, the medical device is introduced into an anatomical structure, such as a heart, and the position of the medical device is detected within this anatomical structure.

The method further comprises automatically activating imaging of the patient based on the detected relative position. Although the present inventions should not be so limited in their broadest aspects, the automatic activation of the imaging facilitates the imaging of tissue only during relevant times, thereby reducing radiation exposure. In one method, instability/stability of the medical device is detected, in which case, the imaging is automatically activated when the medical device is unstable, and deactivated when the medical device is stable. Another method comprises ablating tissue with the medical device, and performing position detection and imaging activation steps during the tissue ablation step. In this manner, medical personnel can be made aware of inadvertent movement of the medical device via the image, and can correct any displacement of the medical device from the ablation site. An optional method comprises automatically adjusting a position of a field of view of the imaging relative to the patient based on the detected position. In this manner, the method not only facilitates imaging of the tissue region during relevant times, it also facilitates imaging of only the relevant tissue.

In accordance with a fifth aspect of the present inventions an imaging system is provided. The system comprises a tissue imaging device, an intrabody medical device, a tracking subsystem configured for detecting a position (e.g., location and/or orientation) of the medical device, and an imager activating subsystem configured for comparing the detected medical device position to a reference position (e.g., a previously detected position of the medical device or a position within a desired path), and activating the imaging device based on the comparison. As with the previously described method, the activation of the imaging device based on the position of the medical device facilitates the imaging of tissue only during relevant times.

In one system, the imager activating subsystem detects the instability/stability of the medical device based on the comparison, in which case, it can activate imaging when the medical device is unstable, and deactivate imaging when the medical device is stable. If the medical device carries a tissue ablation element, the stability/instability of the medical device can be detected during the ablation process, as discussed in the previous method above. In an optional embodiment, the system comprises an imager positioning subsystem configured for automatically adjusting a position of a field of view of the imaging device relative to a patient based on the detected medical device position. As previously discussed above, this provides the added advantage of limiting the imaging to only relevant tissue.

In accordance with a sixth aspect of the present inventions, an imaging system is provided. The imaging system comprises a tissue imaging device, such as the imaging device described above, a processor configured for comparing a detected position of a medical device to a reference position, and a controller configured for activating the imaging device based on the comparison. The detected medical device position can be compared to the reference position, and the imager can be activated in the same manner described above.

Other objects and features of the present invention will become apparent from consideration of the following description taken in conjunction with the accompanying drawings.

BRIEF DESCRIPTION OF THE DRAWINGS

The drawings illustrate the design and utility of preferred embodiments of the present inventions in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 2 is a plan view of a mapping/ablation catheter used in the navigation system of FIG. 1;

FIG. 3 is a perspective view of an imaging subsystem used in the navigation system of FIG. 1;

DETAILED DESCRIPTION OF THE PREFERRED EMBODIMENTS

Figure 1:
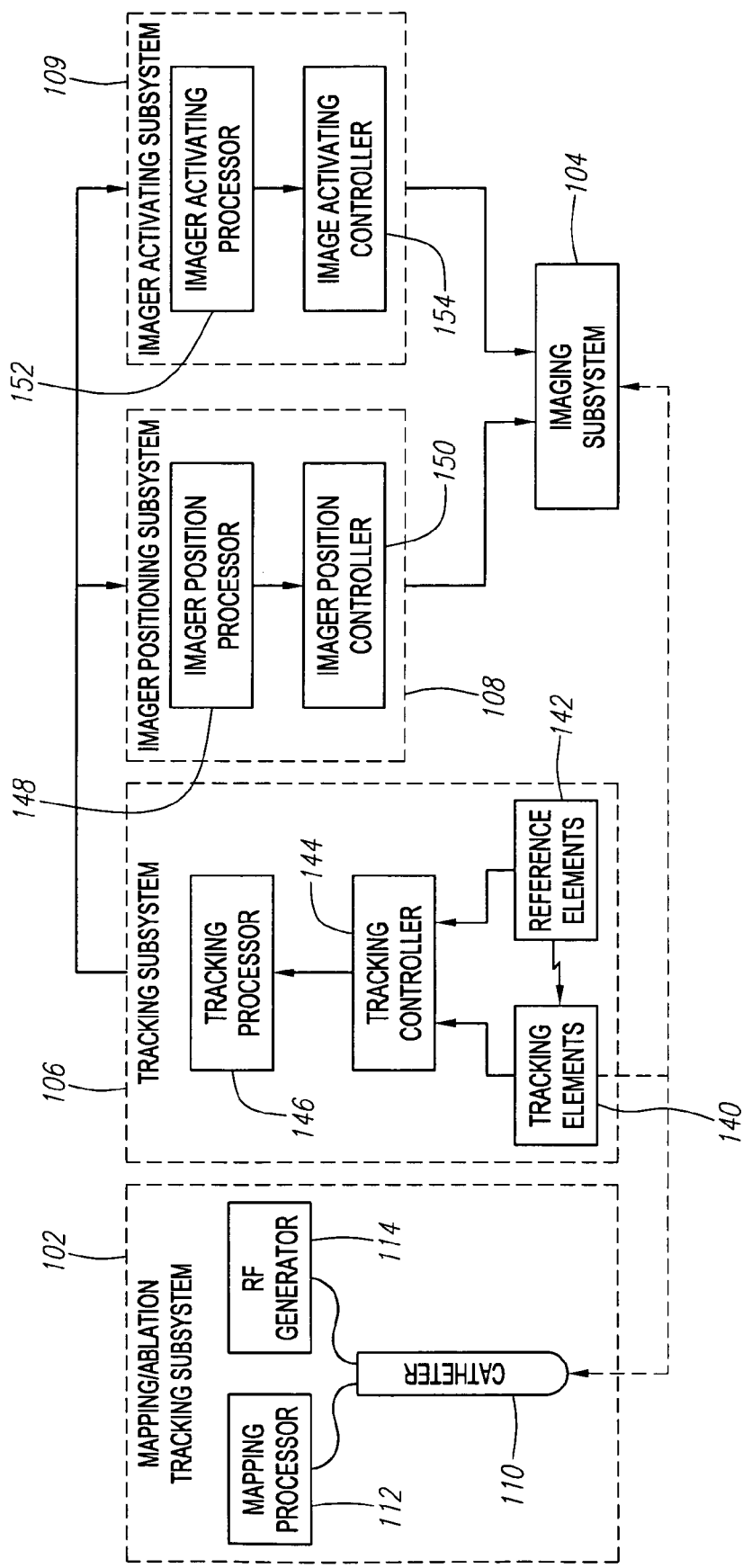
FIG. 1 is a functional block diagram of one preferred embodiment of a medical navigation system constructed in accordance with the present inventions.

Referring to FIG. 1, an exemplary medical navigation system 100 constructed in accordance with the present inventions will be described. The navigation system 100 is particularly suited for intravascularly navigating catheters used to perform intracardiac electrophysiology procedures, but can be used for navigating other catheters, such as angiograph and angioplasty catheters, as well as other medical devices, within a patient's body, including non-vascular medical devices.

The medical system 100 generally comprises (1) a mapping/ablation subsystem 102 for mapping and ablating tissue within the heart; (2) an imaging subsystem 104 for generating medical images of select regions of the patient's body; (3) a tracking subsystem 106 for tracking movable objects, such as catheters and the imaging components of the imaging subsystem 104; (4) an imager positioning subsystem 108 for mechanically manipulating the imaging subsystem 104 based on tracking information acquired from the tracking subsystem 106, such that only the relevant regions of the patient are imaged; and (5) an imager activating subsystem 109 for activating the imaging subsystem 104 based on tracking information acquired from the tracking subsystem 106, such that the patient is imaged only during relevant times. It should be noted that the elements illustrated in FIG. 1 are functional in nature, and are not meant to limit the structure that performs these functions in any manner. For example, several of the functional blocks can be embodied in a single device, or one of the functional blocks can be embodied in multiple devices. Also, the functions can be performed in hardware, software, or firmware.

I. Mapping/Ablation Subsystem

The mapping/ablation subsystem 102 is configured to identify and treat target tissue sites, e.g., aberrant conductive pathways. To this end, the mapping/ablation subsystem 102 comprises a mapping/ablation catheter 110, a mapping processor 112, and a radio frequency (RF) generator 114.

As illustrated in FIG. 2, the mapping/ablation catheter 110 comprises an elongate catheter shaft 116, a plurality of electrodes 118 (in this case, four) carried at the distal end of the catheter shaft 114, and a handle 120 carried at the proximal end of the elongate shaft 114. All four electrodes 118 on the catheter shaft 116 are configured to detect electrical signals in the myocardial tissue of the heart for subsequent identification of target sites. The electrode 118 at the distal tip of the catheter shaft 116 is also configured to be used as an ablation electrode to provide ablation energy to the targeted sites when placed adjacent thereto and operated. The handle 120 includes an electrical connector (not shown) for electrical coupling to the mapping processor 112 and RF generator 114.

Referring back to FIG. 1, the mapping processor 112 is configured to derive activation times and voltage distribution from the electrical signals obtained from the electrodes 118 to determine irregular electrical signals within the heart, which can then be graphically displayed as a map. Mapping of tissue within the heart is well known in the art, and thus for purposes of brevity, the mapping processor 112 will not be described in further detail. Further details regarding electrophysiology mapping are provided in U.S. Pat. Nos. 5,485,849, 5,494,042, 5,833,621, and 6,101,409, which are expressly incorporated herein by reference.

The RF generator 114 is configured to deliver ablation energy to the ablation electrode (i.e., the distal most electrode 118) in a controlled manner in order to ablate sites identified by the mapping processor 112. Alternatively, other types of ablative sources besides the RF generator 114 can be used, e.g., a microwave generator, an acoustic generator, a cryoablation generator, and a laser or other optical generator. Ablation of tissue within the heart is well known in the art, and thus for purposes of brevity, the RF generator 114 will not be described in further detail. Further details regarding RF generators are provided in U.S. Pat. No. 5,383,874, which is expressly incorporated herein by reference.

In an optional embodiment, a robotically-controlled catheter manipulator (not shown) is provided for manipulating the catheter 110 with a plurality of degrees of freedom (e.g., longitudinal, rotational, articulation, etc.). For example, the catheter manipulator can have a motorized slave device for receiving the proximal end of the catheter 110, and a master device that can be manipulated by a user (e.g., via a joystick) to control the slave device, and thus movement of the catheter 110.

II. Imaging Subsystem

Referring to FIG. 3, the imaging subsystem 104 comprises a C-arm fluoroscopic imaging device 122 for acquiring image information of the relevant tissue of a patient, an image console 124 for controlling and acquiring image information from the imaging device 122 and displaying the information to medical personnel as a two-dimensional fluoroscopic image, and a table 126 on which the patient is placed during the imaging process. It can be appreciated that although these elements are illustrated as being mechanically separate from each other, any combination of these elements can be integrated with each other.

The imaging device 122 comprises a C-arm mount 128, an X-ray source 130 mounted to one end of the C-arm 128, and an image acquisition module 132 mounted to the other end of the C-arm 128 opposite the X-ray source 130. The table 126 is configured for positioning the region of the patient to be imaged between the ends of the C-arm 128, and thus, between the X-ray source 124 and the image acquisition module 126. Thus, the X-ray source 130, under control of the imaging console 124, emits x-rays, which transit through the desired tissue region of the patient, and the image acquisition module 132 converts the tissue modulated x-rays into electrical signals, which are representative of two-dimensional images of the tissue. The image console 124 receives the tissue representative electrical signals from the image acquisition module 132 and displays a two-dimensional fluoroscopic image of the relevant tissue to the medical personnel. In the illustrated embodiment, the imaging device 122 has a field of view with a direction of view defined by the size and orientation of the aperture of the imaging device 122, and in this case, the aperture of the image acquisition module 132 that receives the x-rays. The imaging console 124 can operate the imaging device 122 either in a "continuous mode," whereby x-rays are continuously transmitted between the X-ray source 130 and image acquisition module 132 until inactivated by medical personnel, or in a "pulsed mode," whereby x-rays are periodically transmitted between the X-ray source 130 and image acquisition module 132, thereby limiting radiation exposure to the patient and medical personnel. As will be described in further detail below, the imaging activating subsystem 109 (illustrated in FIG. 1) allows the imaging device 122 to be operated in a "dynamic mode," so that the tissue region is only imaged during relevant times.

The imaging device 122 further comprises a motor/drive unit 134 on which the C-arm 128 is supported via a pivot assembly 136, and a base 138 on which the motor/drive assembly case 134 is mounted. The motor/drive assembly unit 134 is configured for actuating movement of the C-arm 128 within a local imaging coordinate system (x', y', z', θ', φ', ρ'). In particular, the motor/drive assembly unit 134 can actuate the pivot assembly 140 to pivot the C-arm 128 about three orthogonal axes (pitch (θ'), roll(φ'), and yaw(ρ')) to allow imaging of the patient from several different angles. Typical fluoroscopic views include anterior-posterior (0° pitch, 0°/180° roll), lateral (90°/−90° pitch, 0° roll), and anterior oblique (45°/−45° pitch, 0° roll). In addition, the motor/drive unit 134 is configured to rectilinearly translate the C-arm 128 in three-dimensional space (e.g., in x'-, y'-, and z'-directions), so that, given a set angular orientation of the C-arm 128, the desired region of the patient to be imaged can be located within the field of view of the imaging device 122. In the illustrated embodiment, the motor/drive unit 134 is coupled to the base 138 via a translational assembly (not shown). In this manner, the motor/drive unit 134 can move relative to the base 138 to effect rectilinear translation of the C-arm 128 in the x'- and y'-directions. The motor/drive unit 134 can move the pivot assembly 136 up and down to effect rectilinear translation of the C-arm 128 in the z'-direction. Alternatively, the patient table 126, instead of, or in addition to, the C-arm 128, can be configured to be rectilinearly translated.

As will be described in further detail below, the motor/drive unit 134 may be automatically controlled by the imager positioning subsystem 108 in order to more efficiently image the relevant regions of the patient.

III. Tracking Subsystem

Referring still to FIG. 1, the tracking subsystem 106 provides a means for tracking the positions (e.g., location and/or orientation) of the catheter 110 and C-arm 128 within an absolute coordinate system (x, y, z, θ, φ, ρ) (illustrated in FIG. 3), which positions will ultimately be used to dynamically adjust the field of view of the imaging device 122, so that the relevant tissue regions of the patient's body can be automatically imaged, as will be described in further detail below. In the illustrated embodiment, the tracking subsystem 106 provides a non-fluoroscopic means for tracking the catheter 110 and C-arm within the absolute coordinate system.

To this end, the tracking subsystem 106 includes (1) a plurality of tracking elements 140 (in this case, two); (2) a plurality of reference elements 142; (3) a controller 144 for coordinating the transmission of signals between the tracking elements 140 and a plurality of reference elements 142; and (4) a processor 146 for determining the positional coordinates (x, y, z) and orientation (pitch(θ), roll(φ), and yaw(ρ)) of the tracking elements 140 within the three-dimensional coordinate system based on the transmitted signals between the tracking elements 140 and reference elements 142. Although the tracking controller 144 and tracking processor 146 are illustrated as being separate from the imager subsystem 104, these components can be conveniently incorporated into the image console 124 illustrated in FIG. 3.

In the illustrated embodiment, the tracking subsystem 106 is magnetically-based, and thus, the tracking elements 140 and reference elements 142 take the form of magnetic coils, which are well-suited for serving as transmitters or receivers. As shown in FIG. 2, one of the tracking elements 140 is physically carried by the distal end of the mapping/ablation catheter 110. Details regarding the incorporation of magnetic tracking elements into catheter structures are disclosed in U.S. Pat. No. 6,740,083, which is expressly incorporated herein by reference. As shown in FIG. 3, the other tracking elements 140 are physically carried by the relevant moving components of the imaging subsystem 104, and in particular, the C-arm 128. Details regarding the mounting of magnetic tracking elements on C-arms and other components are disclosed in U.S. Pat. No. 6,619,838, which is expressly incorporated herein by reference. The reference elements 142 are placed externally from the patient within the operating room in any fixed location that allows communication with the tracking elements 140.

Magnetic tracking techniques are well-known in the prior art, and thus, will not be described in detail herein. For example, the magnetic techniques described in U.S. Pat. Nos. 5,377,678, 6,233,476, 6,484,118, and 6,711,429, the disclosures of which are expressly incorporated herein by reference, can be utilized to determine the locations of the tracking elements 140 within the three-dimensional coordinate system. Other types of non-fluoroscopic tracking means besides those that are magnetically-based can be utilized. For example, the tracking means can be based on ultrasound ranging, voltage gradient measurements, or impedance measurements. The tracking means can alternatively be capable of monitoring the kinematics of the optional robotically controlled catheter manipulator to determine the position of the catheter 110. In the case of the C-arm 128, it can be alternatively tracked based on a known geometry of the C-arm 128 and by monitoring the degree of actuation of the motor/drive unit 134.

The tracking subsystem 106 may optionally comprise memory (not shown) for storing previous locations of the catheter 110, such that the imaging device 122 can be made to return to selected prior locations (for the purpose of imaging those locations), or can be made to move back along a path taken by the catheter 110.

IV. Imager Positioning Subsystem

Referring back to FIG. 1, the imager positioning subsystem 108 is configured for adjusting the field of view of the imaging device 122 relative to the patient, so that only the relevant tissue region of the patient is being imaged at any given time. To this end, the imager positioning subsystem 108 comprises an imager position processor 148 for continuously determining the desired position of the imaging device 122 (and in particular, the C-arm 128) that will place the relevant tissue region of the patient within the field of view (which presumably will change as the position of the catheter 110 within the patient changes), and an imager position controller 150 for placing the C-arm 128 within the determined position via operation of motor/drive unit 134 of the imaging device 122. Although the imager position processor 148 and imager position controller 150 are illustrated as being separate from the imager subsystem 104, these components can be conveniently incorporated into the image console 124 illustrated in FIG. 3.

Figure 4:
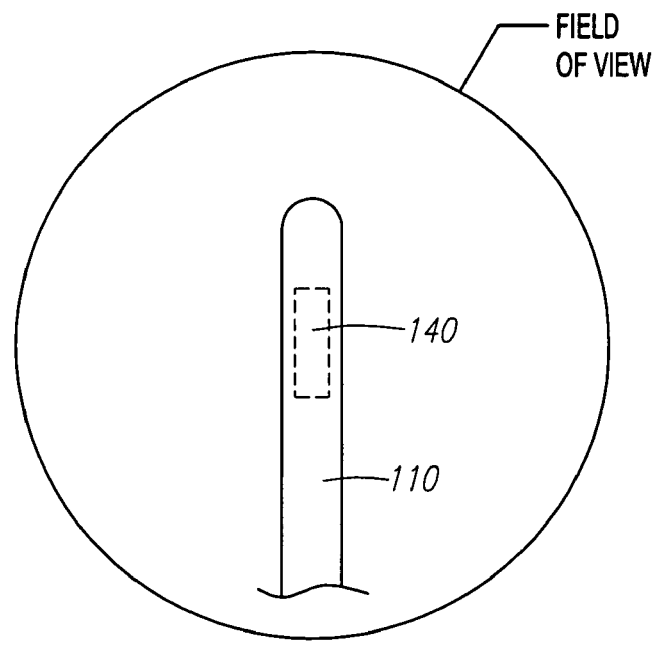
FIG. 4 is a plan view of a field of view of the imaging subsystem of FIG. 3 centered over the distal end of the catheter of FIG. 2.
Figure 5:
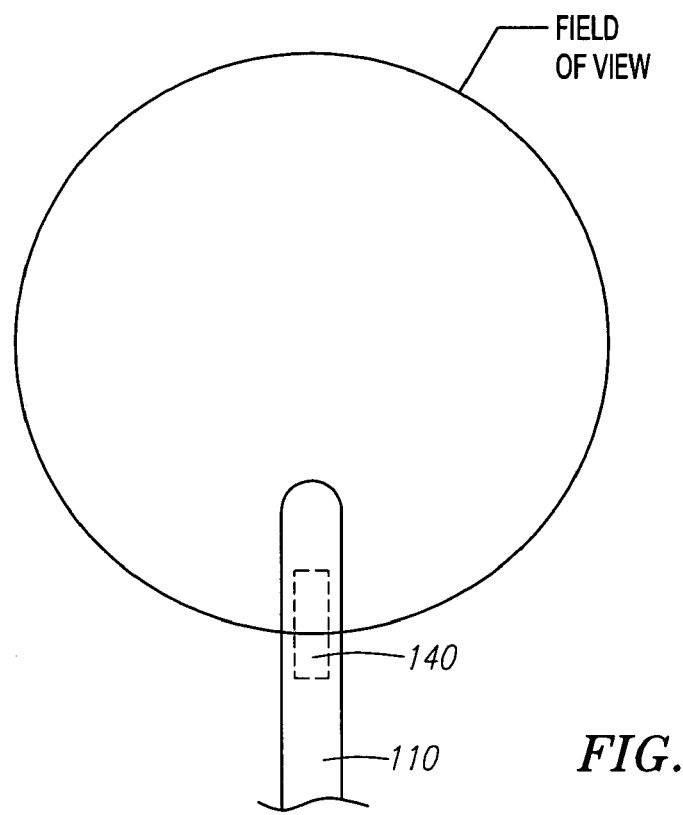
FIG. 5 is a plan view of a field of view of the imaging subsystem of FIG. 3 centered in front of the distal end of the catheter of FIG. 2.
Figure 6:
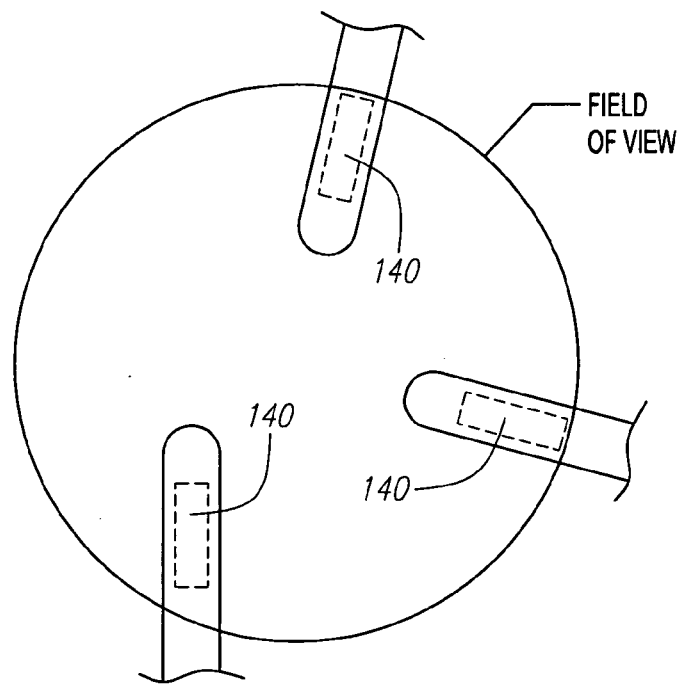
FIG. 6 is a plan view of a field of view of the imaging subsystem of FIG. 3 centered on the geometric center of the distal ends of the multiple catheters.

In this embodiment, the imager positioning subsystem 108 adjusts the field of view of the imaging device 122 based on the determined location parameters (x, y, z) of the catheter tracking element 140 within the absolute coordinate system, such that the field of view moves as the catheter 110 moves relative to the absolute coordinate system, which will typically occur when the catheter 110 is moved within the patient, such as during a catheterization process, but may also occur during movement of the patient, such as the natural movement caused by the patient's respiratory or cardiac cycle. In the illustrated embodiment, it is assumed that the relevant tissue to be imaged will be the tissue that surrounds the distal end of the catheter 110 at it is moved within the patient. Thus, the imager positioning subsystem 108 adjusts the field of view, such that it is always centered over the catheter tracking element 140 (i.e., the center of the field of view intersects the tracking element 140), as illustrated in FIG. 4. Alternatively, it may be assumed that the relevant tissue to be imaged will be the tissue just distal to the catheter 110 (i.e., it may sometimes be desirable to view the tissue in front of the catheter 110, e.g., when approaching a vessel branch during the catheterization process, so that the catheter 110 can be properly manipulated prior to it reaching the imaged tissue region), in which case, the imager positioning subsystem 108 adjusts the field of view, such that it is always centered a distance (e.g., a few inches) in front of (or distal to) the catheter 110, as illustrated in FIG. 5. In an optional embodiment, wherein it is desired to image multiple catheters that are in proximity to each other, the imager positioning subsystem 108 may adjust the field of view, such that it is always centered over a geometric center of the multiple catheters, as illustrated in FIG. 6.

In any event, the position processor 148 acquires the absolute location parameters (x, y, z) of the catheter tracking element 140 from the tracking subsystem 106, and then calculates, using simple trigonometric functions, the position of the C-arm 128 necessary to center the field of view of the imaging device 122 over the targeted tissue region to be imaged (i.e., aligning the center of the field of view with the center of the targeted tissue region), whether it be the tissue surrounding the distal end of the catheter 110 or the tissue just in front of the catheter 110. In the illustrated embodiment, it is assumed that the field of view of the imaging device 122 is centered over the targeted tissue region when the boresight of the image acquisition module 132 (i.e., the line perpendicular to and extending from the imaging aperture) intersects the center of the targeted tissue region.

Because both the targeted tissue region and C-arm are registered within the absolute coordinate system by virtue of the tracking elements 140, the position processor 148 is capable of correlating the position of the C-arm 128 with that of the targeted tissue region. In particular, the position processor 148 determines the correct position of the C-arm 128 by first transforming the acquired absolute location parameters (x, y, z) of the catheter tracking element 140 into location parameters (x', y', z') within the local imaging coordinate system. In the illustrated embodiment, the position processor 148 calculates the transformation function between the absolute and local coordinate systems in a standard manner based on a comparison between the acquired position parameters (x, y, z, $\theta$, $\phi$, $\rho$) of the C-arm tracking element 140 within the absolute coordinate system and known position parameters (x', y', z', $\theta$', $\phi$', $\rho$') of the C-arm tracking element 140 within the local coordinate system. This transformation function can then be applied to the acquired absolute location parameters (x, y, z) of the catheter tracking element 140 to obtain the local imaging location parameters (x', y', z') of the catheter tracking element 140. The position processor 148 then determines the position of the C-arm 128 (which is registered within the local imaging coordinate system) required to center the field of view (as defined by the boresight of the imaging aperture) over the absolute location parameters (x, y, z) of the catheter tracking element 140, or alternatively, some fixed distance from this absolute location.

It should be noted that once the reference elements 142 and imaging subsystem 104 are setup, the relationship between the absolute and local coordinate systems will remain fixed. As such, the C-arm 128 need only be registered within the absolute coordinate system once. That is, the absolute position parameters (x, y, z, $\theta$, $\phi$, $\rho$) of the C-arm tracking element 140 need only be acquired once at the beginning of a procedure to determine the transformation function between the absolute and local coordinate systems. However, to compensate for any dynamic conditions that may occur, such as movement of one or more of the reference elements 142, the absolute position parameters (x, y, z, $\theta$, $\phi$, $\rho$) of the C-arm tracking element 140 can be acquired several times throughout a procedure. In alternative embodiments, the C-arm 128 may be manually registered in the absolute coordinate system without the use of a C-arm tracking element 140. In these cases, however, mechanical precision in setting the reference elements 142 and imaging subsystem 104 is required, and therefore, such an implementation is not desired in situations where the reference elements 142 and imaging subsystem 104 are designed to be moved about the operating room.

It should also be noted that, in the configuration described above, the position processor 148 calculates the desired position of the C-arm 128 in an open-looped fashion. That is, the position processor 148 assumes that if the C-arm 128 is placed within a nominal position, the field of view of the imaging device 122 will be centered over a known point within the local coordinate system. That is, the field of view of the imaging device 122 is correlated to nominal positions of the imaging device 122. However, the position processor 148 can alternatively calculate the desired position of the C-arm 128 in a closed-loop fashion by using the transformed local position parameters (x', y', z', $\theta$', $\phi$', $\rho$') of the C-arm tracking element 140 as an error signal throughout the process. In this case, the position processor 148 does not calculate nominal local positions of the C-arm 128, but rather calculates the differences between the local position of the current C-arm tracking element 140 and a subsequent position of the C-arm tracking element 140 necessary to center of the field of view over the targeted tissue region. The position processor 148 then calculates the local positional changes in the C-arm 128 necessary to effect this difference. In this manner, any misregistration of the imaging device 122 within the local coordinate system, or otherwise any error in the predicted position of the imaging device 122, will be eliminated, or at least minimized.

It should also be noted that because the position processor 148 can adjust six local positional parameters (x', y', z', $\theta$', $\phi$', $\rho$') of the imaging device 122 to center the field of view over a point defined by three location parameters (x', y', z'), the position controller 150 can theoretically position the imaging device 122 in an infinite number of ways. However, medical personnel will typically set the C-arm 128 to a desired angular orientation, in which case, the position processor 148 need only calculate the local location parameters (x', y', z') of the C-arm 128 necessary to center the field of view over the targeted tissue region.

For example, if the imaging device 122 is configured to provide an anterior or posterior view of the tissue, the C-arm 128 can be rectilinearly translated, such that the local x'- and y'-coordinates of the center of the field of view matches the local x'- and y'-coordinates of the center of the desired tissue region to be imaged (e.g., the local x'- and y'-coordinates of the catheter tracking element 140 or a region in front of the catheter tracking element 140). In contrast, if the imaging device 122 is configured to provide left or right lateral views, the C-arm 128 can be rectilinearly translated, such that the local y'- and z'-coordinates of the center of the field of view matches the local y'- and z'-coordinates of the center of the desired tissue region to be imaged (e.g., the local y'- and z'-coordinates of the catheter tracking element 140 or a region in front of the catheter tracking element 140).

Notably, in the particular scenarios illustrated above wherein the C-arm 128 is oriented orthogonally with respect to the local coordinate system, it can be assumed that the local x'- and y'-coordinates of the center of the field of view will match the local x'- and y'-coordinates of the center of the imaging aperture (in the case of an anterior or posterior view), or that the local y'- and z'-coordinates of the field of view will match the local y'- and z'-coordinates of the center of the imaging aperture (in the case of a left or right lateral views). In these cases, the coordinates of the center of the imaging aperture need only be matched with the coordinates of the center of the desired tissue region. In cases where the C-arm 128 is oriented non-orthogonally with respect to the local coordinate system, such as when anterior oblique views are desired, the desired rectilinear coordinates of the center of the imaging aperture can be calculated using a simple trigonometric function of the local orientation parameters ($\theta$', $\phi$', $\rho$') of the C-arm 128 and the local location parameters (x', y', z') of the center of the targeted tissue region.

It should also be noted that, although the C-arm 128 has been described as being moved to place the field of view of the imaging device 122 over the targeted tissue region, as previously mentioned, the position processor 148 may alternatively calculate the desired position of the patient table 126 that will place the relevant tissue region of the patent within the field of view, in which case, the position controller 150 will be configured for placing the patient table 126 within the determined position via operation of a motor/drive unit (not shown) associated with the patient table 126. For example, given a set orientation of the C-arm 128, the patient table 126 may be rectilinearly translated in the x', y', and z'-directions.

Figure 7:
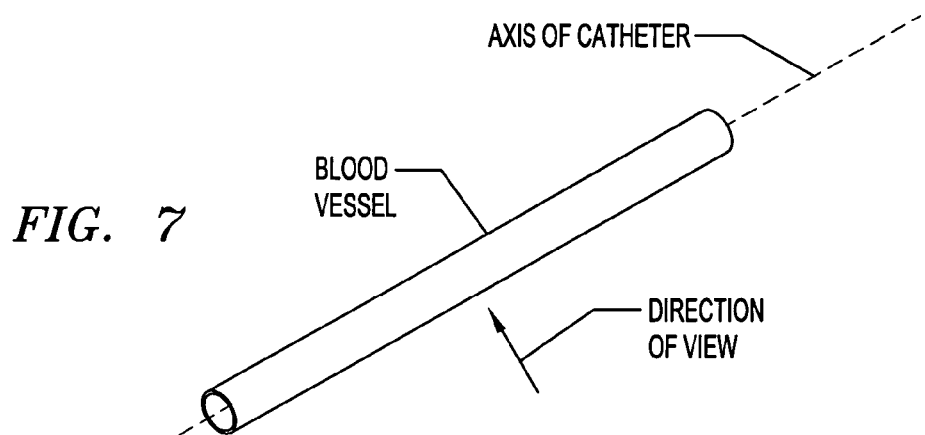
FIG. 7 is a perspective view of a imaging direction of the imaging subsystem of FIG. 3 oriented perpendicular to the axis of the catheter of FIG. 2.
Figure 8:
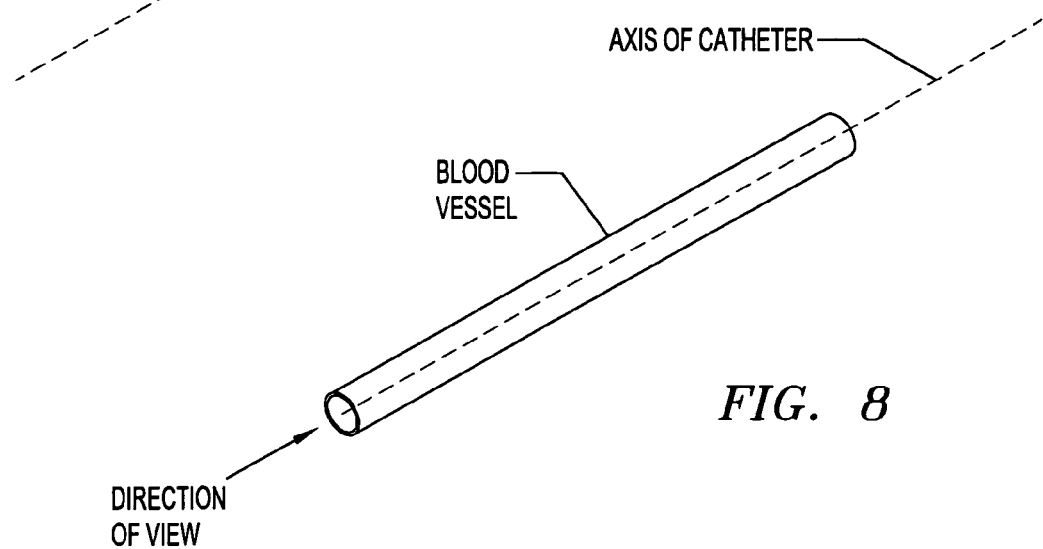
FIG. 8 is a perspective view of a imaging direction of the imaging subsystem of FIG. 3 oriented parallel to the axis of the catheter of FIG. 2.

Although it has been assumed that all three local orientation parameters (θ', φ', ρ') will be set by medical personnel, the system 100 may be configured, such that one or more of these orientation parameters are calculated by the position processor 148. For example, it may sometimes be desirable to make the imaging direction perpendicular to the orientation of the catheter tracking element 140, and in particular, to the axis of the distal end of the catheter 110, as illustrated in FIG. 7. Such a function may be useful, e.g., to more accurately judge the lengths of anatomical structures, such as blood vessels. It may also sometimes be desirable to make the imaging direction parallel to the orientation of the catheter tracking element 140, and in particular, the axis of the distal end of the catheter 110, as illustrated in FIG. 8. Such a function may be useful, e.g., to allow accurate angiographic measurement of the diameter of the channel through which the catheter 100 is being navigated.

In these cases, the position processor 148 acquires the absolute orientation parameters of the catheter tracking element 140 (i.e., the absolute orientation parameters (θ, φ, ρ) in addition to the absolute location parameters (x, y, z)), transforms the absolute position parameters into position parameters (x', y', z', θ', φ', ρ') within the local imaging coordinate system using a transformation function, as calculated above, and based on these local position parameters, determines the position of the C-arm 128 necessary to both center the field of view of the imaging device 122 over the targeted tissue region to be imaged, and to orient the imaging direction relative to the orientation of the catheter tracking element 140 (e.g., perpendicular or parallel), and in this case, with the axis of the catheter 110.

As briefly discussed above, the position processor 148 transmits signals to the position controller 150, which changes the position of the imaging device 122 in accordance with these signals. In the illustrated embodiment, the position controller 150 continuously adjusts the position of the C-arm 128, so that the field of view is always centered on the targeted tissue region. Alternatively, the position controller 150 only adjusts the position of the C-arm 128 to center the field of the field on the targeted tissue region when prompted by medical personnel, i.e., in an "on-demand" mode.

V. Imager Activating Subsystem

Referring back to FIG. 1, the imager activating subsystem 109 is configured for operating the imaging subsystem 104 in a "dynamic mode," in addition to the "continuous" and "pulse" modes described above. In the dynamic mode, radiation is only transmitted between the x-ray source 130 and image acquisition module 132 of the imaging device 122 during relative times, and in particular, when the catheter 110 moves (e.g., during the catheterization process or when the catheter 110 inadvertently moves from a target position (such as an ablation site) or from a target path), in order to minimize the amount of radiation to which the patient and medical personnel is exposed. To this end, the imager positioning subsystem 108 comprises an imager activation processor 152 for continuously comparing the current position of the catheter 110 to the previous position of the catheter 110, and an imager actuation controller 154 for selectively activating and inactivating the imaging device 122 based on the position comparison. Although the imager activating processor 152 and imager activating controller 154 are illustrated as being separate from the imager subsystem 104, these components can be conveniently incorporated into the image console 124 illustrated in FIG. 3.

In the illustrated embodiment, the imager activating subsystem 109, during the "dynamic mode," activates the imaging device 122 when substantial movement of the catheter 110 is detected, and deactivates the imaging device 122 when substantial movement of the catheter 110 is not detected. In particular, the activation processor periodically acquires the absolute location parameters (x, y, z) of the catheter tracking element 140 from the tracking subsystem 106, and compares the currently acquired absolute location parameters with the previously acquired location parameters. The activation processor 152 then compares this difference to a threshold value to determine if the catheter tracking element 140, and thus the catheter 110, is moving. If the location parameter difference surpasses the threshold value, the activation processor 152 sends an activation signal to the activation controller 154, which will activate the imaging device 122, if currently deactivated. If the location parameter difference does not surpass the threshold value, the activation processor 152 sends a deactivation signal to the activation controller 154, which will deactivate the imaging device 122, if currently activated.

Although only movement of the catheter 110 as represented by a change in the absolute location parameters (x, y, z) of the catheter tracking element 140 has been described as prompting activation of the imaging device 122, the movement of the catheter 110 as represented by a change in the absolute orientation parameters (θ, φ, ρ) of the catheter tracking element 140 can be used to prompt activation of the imaging device 122.

In an alternative embodiment, the imager activating subsystem 109, during the "dynamic mode," activates the imaging device 122 when the catheter 110 has strayed from a desired path. In this case, the activation processor 152 acquires the absolute location parameters (x, y, z) of the catheter tracking element 140, but instead of comparing them to the previously acquired absolute location parameters, the activation processor 152 compares them to the absolute location parameters (x, y, z) of the desired path that are closest to the currently acquired location parameters of the catheter tracking element 140.

Notably, the absolute location parameters of the desired path can be defined by, e.g., using a mouse to define the desired path on a graphical display of the pertinent tissue or by defining the desired path with the tip of the catheter 110 or another catheter that includes a tracking element 140. Details describing the definition of desired paths in three-dimensional coordinate systems are set forth in U.S. patent application Ser. No. 11/002,629, entitled "System and Use Thereof To Provide Indication of Proximity Between Catheter and Location of Interest in 3-D Space," which is hereby expressly incorporated herein by reference.

If the difference between the current location parameters of the catheter tracking element 140 and the closest location parameters of the defined track surpasses a threshold value, the activation processor 152 sends an activation signal to the activation controller 154, which will activate the imaging device 122, if currently deactivated. If the location parameter difference does not surpass the threshold value, the activation processor 152 sends a deactivation signal to the activation controller 154, which will deactivate the imaging device 122, if currently activated. Notably, it may be desirable to compare the location parameters (x, y, z) of the catheter tip (e.g., during an ablation process), rather than the location parameters (x, y, z) of the location element 140, with the location parameters (x, y, z) of the desired path. In this case, the location parameters of the catheter tip can be determined by extrapolating the acquired location parameters (x, y, z) of the tracking element 140 based on the known geometry of the catheter 110 and the known distance between the catheter tip and location element 140.

In the cases described above, the imaging device 122 is activated in a continuous manner during movement of the catheter 110 (i.e., the imaging device 122 is activated as long as the catheter 110 remains moving, and is deactivated when the catheter 110 stops moving), which should be distinguished from the "continuous mode," wherein the imaging device 122 is continuously activated irrespective of catheter movement. In alternative embodiments, the imager activating subsystem 109, during the "dynamic mode," activates the imaging device 122 only for a brief period of time (e.g., for one second) when substantial movement of the catheter 110 is detected. In this case, if the threshold value is surpassed, the activation processor 152 sends an activation signal to the activation controller 154, which will activate the imaging device 122 for a period of time and then deactivate the imaging device 122 when the time period has expired. If the threshold value is not surpassed, the activation processor 152 will not activate the imaging device 122 at all. In this manner, the imaging device 122 is activated in a pulsed manner during movement of the catheter 110, which should be distinguished from the "pulse mode," wherein activation of the imaging device 122 is pulsed irrespective of catheter movement.

It should be noted that a tracking element may optionally be affixed to the patient in order to sense patient movement (e.g., movement of the chest during the respiratory cycle) that may otherwise falsely trigger activation of the imaging device 120 prompted by the associated movement of the catheter tracking element 140. That is, the activation processor 152 may compensate for patient movement by acquiring the relevant position parameters (location and/or orientation parameters) from the patient tracking element (not shown) and subtracting these position parameters from the respective position parameters acquired from the catheter tracking element 140 prior to performing the calculations described above. Alternatively, rather than providing a separate patient tracking element, the position parameters of the catheter tracking element 140 may be acquired only during a certain time within the respiratory and/or cardiac cycle to substantially eliminate the adverse effects of patient movement.

VI. Method of Use

Figure 9:
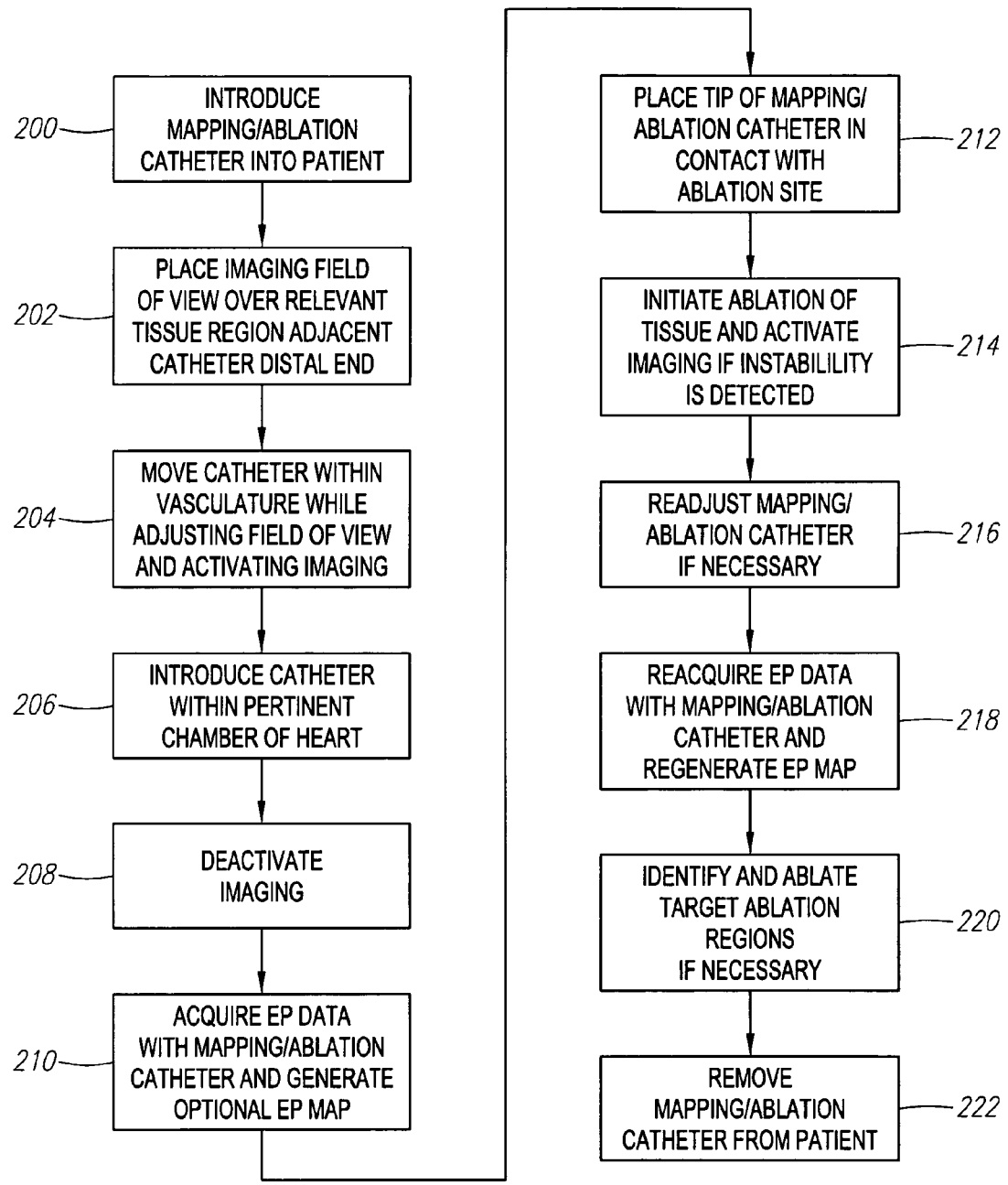
FIG. 9 is a flow diagram illustrating a method of treating an aberrant conductive path using the navigation system of FIG. 1.

Having described the structure of the medical system 100, one method of using the system 100 to locate and treat an aberrant conductive pathway within the heart, such as those typically associated with atrial fibrillation, will now be described with reference to FIG. 9. The medical system 100 can be used in conjunction with a three-dimensional navigation system, such as the RPM or CARTO EP systems.

First, the catheter 110 is introduced into the patient via an access point, such as within the femoral vein and artery (step 200). Next, the imaging subsystem 104 and tracking subsystem 106 are operated, so that the imaging device 122 is positioned to initially place the field of view over the relevant tissue region adjacent the distal end of the catheter 110 (step 202). That is, the imager positioning subsystem 108 automatically determines the position parameters (x, y, z, θ, φ, ρ) of the catheter tracking element 140, and thus, the distal end of the catheter 110, within the absolute coordinate system, and automatically adjusts the position of field of view of the imaging device 122 relative to the patient (by moving the imaging device 122 and/or patient table 126 within the absolute coordinate system) based on the determined absolute position of the catheter tracking element 140. Notably, the imaging device 122 need not be activated at this point, thereby reducing the amount of radiation to which the patient and medical personnel are exposed.

Next, the catheter 110 is moved through the patient's vasculature (typically, the inferior vena cava or the abdominal aorta), during which the imager positioning subsystem 108 adjusts the field of view position, such that it coincides with the targeted tissue region adjacent the distal end of the catheter 110, and the imaging device 122 is activated to image the targeted tissue region (step 204). The imager position subsystem 108 can either be operated, so that the field of view of the imaging device 122 continuously tracks the targeted tissue region, or can be operated, so that the field of view of the imaging device 122 coincides with the current targeted tissue region only when prompted by the medical personnel ("on-demand), after which it becomes fixed until prompted again. The tissue region may either be imaged in a "continuous mode," during which imaging is activated by the medical personnel, and continues until deactivated by the medical personnel, in a "pulsed mode," during which imaging is activated by the medical personnel, and is pulsed until deactivated by the medical personnel, or in a "dynamic mode," during which the imager activation subsystem 109 detects movement in the catheter 110 and automatically activates imaging if movement is detected, and deactivates imaging if movement is not detected.

The catheter 110 is then introduced into the pertinent chamber of the heart (step 206). In one preferred method, a three-dimensional navigation system is used to graphically reconstruct and display the relevant chamber and catheter 110, in which case, the imaging subsystem 104 can be deactivated manually by the medical personnel in order to minimize radiation exposure (step 208). While the catheter 110 is moved around within the heart chamber, the mapping processor 112 is operated to record electrical activity within the heart and derive mapping data therefrom, and the optional three-dimensional navigation system can then graphically generate and display an electrical activity map (step 210). If an aberrant region is identified, the distal tip of the catheter 110 is placed into contact with the targeted ablation region, and the imaging subsystem 104 is operated in the dynamic mode to ensure that the catheter 110 is stable (step 212). The RF generator 114 is then operated to begin ablating the tissue, and if instability in the catheter 110 is detected by the imager activating subsystem 109, it automatically activates the imaging device 122 to image the tissue adjacent the catheter 110, so that the medical personnel can ensure that the catheter 110 is still properly positioned (step 214), and if not, can readjust the position of the catheter 110 (step 216). After the lesion has been completed, the mapping processor 112 can again be operated to ensure that the heart disease has been successfully treated by reacquiring the mapping data and regenerating the electrical activity map (step 218). If additional aberrant conductive pathways have been found, the target ablation regions are again identified and ablated (step 220). If no aberrant conductive pathways have been found, the catheter 110, and any other catheters, can then be removed from the patient (step 222).

It can be appreciated from the foregoing that the use of the imager positioning subsystem 108 and imager activating subsystem 109 in conjunction with an imaging device, such as fluoroscope, may provide many benefits. As examples, because the field of view of the imaging device automatically tracks the relevant tissue, there is an improved ease-of-use, improved efficiency, reduced operator effort with regard to the operation of the imaging subsystem, and an improved guidance with regard to the manipulation of medical devices. Also, because the field of view is always centered over the relevant tissue, the radiation footprint can be reduced and more focused, thereby improving the relevance of the imaging information, improving the quality of the resulting image, reducing the amount of radiation to which the patient and medical personnel are exposed, and potentially lowering the cost of the imaging device due to lower required power-handling capabilities. Procedure times can therefore be shortened, resulting from better imaging information and less time spent manually adjusting the imaging device. In addition, because the imaging device can be automatically activated/deactivated, so that the tissue is only imaged during relevant times, the amount of radiation to which the patient and medical personnel are exposed is further reduced, and the overall life (or maintenance levels) can be extended due to reduced "on time."

It should be appreciated that although the imaging device 122 has been described as a fluoroscopic imaging device, other types of imaging modalities, such as magnetic resonance imaging (MRI), computed tomography (CT), positron tomography (PET), ultrasound, and optical can be used. Also, although the field of view of the imaging device has been described as being automatically adjusted mechanically, the field of view of imaging devices, such as high resolution ultrasound imaging devices, can be automatically adjusted electronically by, e.g., steering the ultrasound beam. Also, rather than using an external device, such as a fluoroscopic imaging device, an internal imaging device, such as an imaging probe or catheter, can be used.

Also, although the position of the field of view of an imaging device and/or activation/deactivation of the imaging device have been described as being controlled in response to the position of a medical device, such as a catheter, other parameters of the imaging device can alternatively or optionally be controlled in response to the position of the catheter. For example, the geometry of the field of view of the imaging device can be altered, e.g., by controlling the size of the field of view. In one method, at the beginning of the medical procedure when the catheter is first introduced into the patient, the field of view can be relatively broad in order to provide a global view of the patient's body. As the catheter approaches a target location, the field of view can be narrowed to focus it on the catheter and its immediate surroundings. As another example, the intensity of energy transmitted from the imaging device can be adjusted based on the location of the catheter. In one method, the transmitted energy may be adjusted based on the distance between the imaging device and the catheter or the depth of the catheter within the patient (e.g., by decreasing the intensity if the distance or depth is relatively small and increasing the intensity if the distance or depth is relative great).

Although particular embodiments of the present invention have been shown and described, it will be understood that it is not intended to limit the present invention to the preferred embodiments, and it will be obvious to those skilled in the art that various changes and modifications may be made without departing from the spirit and scope of the present invention. Thus, the present inventions are intended to cover alternatives, modifications, and equivalents, which may be included within the spirit and scope of the present invention as defined by the claims.

What is claimed is:

1. A method of navigating a medical device within a patient, comprising:
   imaging the patient within a field of view;
   moving the medical device within the patient;
   detecting a position of the moving medical device; and
   automatically adjusting a position of the field of view relative to the patient based on the detected medical device position, such that every time the medical device moves, the field of view moves simultaneously with the medical device in order to maintain a fixed relative position between the field of view and the medical device.

2. The method of claim 1, wherein the patient is imaged fluoroscopically.

3. The method of claim 1, wherein the patient is imaged externally.

4. The method of claim 1, wherein the medical device is an intravascular catheter.

5. The method of claim 1, wherein the position of the medical device comprises a position of a distal end of the medical device.

6. The method of claim 1, wherein the detected medical device position comprises a detected location of the medical device.

7. The method of claim 1, wherein the detected medical device position comprises a detected orientation of the medical device.

8. The method of claim 1, wherein the position of the medical device is detected in a three-dimensional coordinate system.

9. The method of claim 1, wherein the automatic field of view adjustment comprises adjusting the field of view position relative to a fixed point.

10. The method of claim 1, wherein the automatic field of view adjustment comprises adjusting a position of the patient relative to a fixed point.

11. The method of claim 1, wherein the automatic field of view adjustment comprises centering the field of view over a distal end of the medical device.

12. The method of claim 1, wherein the automatic field of view adjustment comprises centering the field of view on a point distally spaced a predetermined distance from the medical device.

13. The method of claim 1, wherein the patient is imaged along a direction of view, and the automatic field of view adjustment comprises orientating a direction of view at an angle perpendicular to an axis of the medical device.

14. The method of claim 1, wherein the patient is imaged along a direction of view, and the automatic field of view adjustment comprises orientating the direction of view at an angle parallel to an axis of the medical device.

15. The method of claim 1, wherein the field of view position is adjusted mechanically.

16. The method of claim 1, wherein the field of view position is adjusted electronically.

17. The method of claim 1, wherein the imaging is automatically activated based on the detected medical device position.

18. The method of claim 1, wherein the position of the medical device is detected within an absolute coordinate system, and the patient is imaged within a local imaging coordinate system, the method further comprising detecting a position of the field of view within the absolute coordinate system, and registering the local imaging coordinate system and absolute coordinate system based on the detected field of view position.

19. The method of claim 1, further comprising:
   moving another medical device within the patient;
   detecting a position of the other moving medical device; and automatically adjusting the field of view relative to the patient based further on the other detected medical device position.

20. A medical navigation system, comprising:
a tissue imaging device having a field of view;
an intrabody medical device;
a tracking subsystem configured for detecting a position of the medical device; and
an imager positioning subsystem configured for adjusting a position of the field of view based on the detected medical device position, such that every time the medical device moves, the field of view moves simultaneously with the medical device in order to maintain a fixed relative position between the field of view and the medical device.

21. The system of claim 20, wherein the imaging device is a fluoroscopic device.

22. The system of claim 20 wherein the imaging device is configured for external imaging of a patient such that the imaging device is external to the patient.

23. The system of claim 20, wherein the medical device is an intravascular catheter.

24. The system of claim 20, wherein the detected medical device position comprises a detected location of the medical device.

25. The system of claim 20, wherein the detected medical device position comprises a detected orientation of the medical device.

26. The system of claim 20, wherein the imager positioning subsystem is configured for adjusting the field of view position relative to a fixed point.

27. The system of claim 20, wherein the imager positioning subsystem is configured for adjusting a position of a patient relative to a fixed point.

28. The system of claim 20, wherein the imager positioning subsystem is configured for centering the field of view over a portion of the medical device.

29. The system of claim 20, wherein the imager positioning subsystem is configured for centering the field of view on a point distally spaced a predetermined distance from the medical device.

30. The system of claim 20, wherein the imager positioning subsystem is configured for orientating a direction of view of the imaging device at an angle perpendicular to an axis of the medical device.

31. The system of claim 20, wherein the imager positioning subsystem is configured for orientating a direction of view of the imaging device at an angle parallel to an axis of the medical device.

32. The system of claim 20, wherein the imager positioning subsystem is configured for mechanically adjusting the field of view position.

33. The system of claim 20, wherein the imager positioning subsystem is configured for electronically adjusting the field of view position.

34. The system of claim 20, further comprising an imager activating subsystem configured for automatically activating the imaging device based on the detected medical device position.

35. The system of claim 20, further comprising another intrabody medical device, wherein the tracking subsystem is configured for detecting a position of the other medical device, and the imager positioning subsystem is configured for adjusting the field of view further based on the other detected medical device position.

36. The system of claim 20, wherein the tracking subsystem comprises a non-fluoroscopic navigation system.

37. The system of claim 20, wherein the imaging device has a local imaging coordinate system, and the tracking subsystem is configured for detecting the position of the medical device within an absolute coordinate system, detecting a position of the imaging device within the absolute coordinate system, and registering the local imaging coordinate system and absolute coordinate system based on the detected imaging device position.

38. An imaging system, comprising:
a tissue imaging device having a field of view;
a processor configured for determining a desired position of the field of view based on a detected position of an intrabody medical device and a fixed relative position between the field of view and the medical device; and
a controller configured for adjusting the position of the field of view relative to a patient in accordance with the desired field of view position, such that every time the medical device moves, the field of view moves simultaneously with the medical device in order to maintain the fixed relative position.

39. The system of claim 38, wherein the imaging device is a fluoroscopic device.

40. The system of claim 38, wherein the imaging device is configured for external imaging of the patient such that the imaging device is external to the patient.

41. The system of claim 38, wherein the processor is configured for determining the desired position of the field of view based on a detected location of the medical device.

42. The system of claim 38, wherein the processor is configured for determining the desired position of the field of view based on a detected orientation of the medical device.

43. The system of claim 38, wherein the processor is configured for determining the desired field of view position that centers the field of view over a portion of the medical device.

44. The system of claim 38, wherein the processor is configured for determining the desired field of view position that centers the field of view on a point distally spaced a predetermined distance from the medical device.

45. The system of claim 38, wherein the processor is configured for determining the desired field of view position that orients a direction of view of the imaging device at an angle perpendicular to an axis of the medical device.

46. The system of claim 38, wherein the processor is configured for determining the desired field of view position that orients a direction of view of the imaging device at an angle parallel to an axis of the medical device.

47. The system of claim 38, wherein the controller is configured for mechanically adjusting the field of view.

48. The system of claim 38, wherein the controller is configured for electronically adjusting the field of view.

49. The system of claim 38, further comprising another controller configured for automatically activating the imaging device based on the detected medical device position.

* * * * *